United States Patent [19]

Cormier

[11] 4,416,900

[45] Nov. 22, 1983

[54] USE OF N-PHENYL-1-NAPHTHYLAMINE IN THE UTERUS TO PREVENT PREGNANCY

[75] Inventor: Milton J. Cormier, Bogart, Ga.

[73] Assignee: University of Georgia Research Foundation, Inc., Athens, Ga.

[21] Appl. No.: 398,299

[22] Filed: Jul. 14, 1982

Related U.S. Application Data

[60] Division of Ser. No. 253,567, Jul. 6, 1981, Pat. No. 4,377,577, which is a continuation-in-part of Ser. No. 155,800, May 30, 1980.

[51] Int. Cl.³ .............................................. A61K 31/135
[52] U.S. Cl. ............................ 424/330; 424/DIG. 14
[58] Field of Search ...................... 424/330, DIG. 14; 560/431

[56] References Cited

PUBLICATIONS

Kobyashi et al., *Biochemical & Biophysical Research Comm.*, p. 1037, 1979.
LaPorte et al., *Biochemistry*, 1980, p. 3814.
Hidaka et al., *Molecular Pharmacology*, 15, pp. 49, 52, 1978.
Hidaka et al., *Molecular Pharmacology*, 17, p. 66, 1979.
Hidaka et al., *Biochemical & Biophysical Research Comm.*, p. 694, 1979.

*Primary Examiner*—Leonard Schenkman

[57] ABSTRACT

The use of N-phenyl-1-naphthylamine by injecting or introducing such drug directly into the uterus is disclosed as a means of preventing pregnancy after intercourse has occurred. Various means of introducing such drug are disclosed, such as by mixing such drug with jelly carriers, foam carriers, or paraffin oil.

8 Claims, No Drawings

USE OF N-PHENYL-1-NAPHTHYLAMINE IN THE UTERUS TO PREVENT PREGNANCY

This application is a division of application Ser. No. 253,567 filed July 6, 1981 now U.S. Pat. No. 4,377,577, which, in turn, is a continuation-in-part of application Ser. No. 155,800 filed May 30, 1980.

The present invention relates to a method of preventing pregnancy. More specifically, the present invention relates to the use of calmodulin binding drugs as a means to prevent pregnancy after intercourse by injecting such drugs into the uterus.

Presently, there is no effective method or product known for preventing conception or pregnancy after sexual intercourse has occurred, especially after an hour or more has elapsed after intercourse. For the purpose of this application pregnancy is intended to be defined as the implantation of a fertilized egg to the uterus.

Currently, in cases of rape or other cases of intercourse where pregnancy is unwanted, other than using douches or other normally ineffective methods to attempt to prevent conception, the normal practice is to wait to see whether the signs of pregnancy occur and, if so, have an abortion if the pregnancy is to be terminated.

Drugs that are capable of binding with calmodulin only in the presence of calcium are known as calmodulin binding drugs. Psychoactive drugs constitute one class of calmodulin binding drugs. Other known calmodulin binding drugs are disclosed in this application.

DESCRIPTION OF THE INVENTION

The present invention comprises the use of calmodulin binding drugs to prevent pregnancy. The introduction of such drugs into the uterus can be accomplished by normal clinical methods, such as injection by way of the vaginal tract, through the cervix and into the uterus. Such treatment is quick and simple; at least as simple as the currently used procedure for PAP Smears. By introduction of an effective amount or concentration of one or a combination of calmodulin binding drugs into the uterus prior to the implantation of a fertilized egg to the wall of the uterus, pregnancy will be prevented. Calmodulin binding drugs in the uterus will either prevent conception, if it has not yet taken place, or embryonic development of a fertilized egg prior to and necessary for implantation. Since implantation normally does not occur for several days after conception, the present invention may be used effectively for a significant period of time after intercourse, perhaps up to three or four days later.

The present invention does not involve the killing of the sperm, but instead directly and specifically blocks the physiological process of conception and embryonic development. It has been shown in the past few years that there is a regulatory protein known as calmodulin, found in all cells of higher organisms and which is the key to the control of a wide variety of physiological processes. We have found that calmodulin is involved in triggering the activation of mammalian spermatozoa, a prerequisite to the fertilization process, as well as in triggering the early events of ovum development after fertilization has occurred. Calmodulin is a calcium binding protein, which means that when calcium is bound to the protein the resulting calcium-protein complex turns on a variety of cellular processes including spermatozoan or ovum activation. We have found that calmodulin binding drugs inhibit the calmodulin function, and, as a result, use of such drugs will prevent the activation of spermatozoa and will prevent embryonic development following fertilization.

Calmodulin binding drugs are drugs that will bind tightly to calmodulin only in the presence of calcium. The binding of these drugs to calmodulin results in the inhibition of calmodulin function.

The use of an affective calmodulin binding drug in the uterus to prevent pregnancy has a number of advantages. First, it is extremely effective since the specific binding of the drug to calmodulin would turn off spermatozoan or ovum activation and embryonic development and thus prevent pregnancy. Experimental evidence has demonstrated that the phenothiazine drugs penetrate the spermatozoan membranes within seconds and concentrate in the region of the cell occupied by calmodulin. Second, there will be no expected side effects since the drug would not be used internally and since low concentrations will be very effective. Third, the effectiveness of an application may last for hours due to the stability of these drugs.

Known calmodulin binding drugs include the following two classes of compounds. The first class includes, and is exemplified by the following compounds:
 (a) 8-anilino-1-naphthalenesulfonate
 (b) 9-anthroylcholine
 (c) N-phenyl-1-naphthylamine The second class of compounds includes, and is exemplified by the following compounds:
 (a) N-(6aminohexyl)-5-chloro-1-naphthalenesulfonamide
 (b) N-(6 aminohexyl)-5-chloro-2-naphthalenesulfonamide
 (c) N-(6 aminohexyl)-5-bromo-2-naphthalenesulfonamide To accomplish the present invention the calmodulin binding drugs would be combined with an appropriate carrier medium, such as paraffin oil, foam carriers or jelly carriers.

A preferred embodiment of the present invention comprises a buffered two percent concentration of N-phenyl-1-naphthylamine in paraffin oil, introduced into the uterus in sufficient quantity and under known methods within six hours after sexual intercourse has occurred and allowed to remain therein.

What is claimed is:

1. A method of preventing pregnancy in a female which comprises introducing an effective amount of the drug N-phenyl-1-naphthylamine directly into the uterus of the female after sexual intercourse.

2. The method as described in claim 1, wherein the step of introducing N-phenyl-1-naphthylamine comprises introducing a mixture of said drug and a foam carrier directly into the uterus of the female after sexual intercourse by injection means.

3. The method as described in claim 1, wherein the step of introducing N-phenyl-1-naphthylamine comprises introducing a mixture of said drug and a jelly carrier directly into the uterus of the female after sexual intercourse by injection means.

4. The method as described in claim 1, wherein the step of introducing N-phenyl-1-naphthylamine comprises introducing a mixture of said drug and paraffin oil directly into the uterus of the female after sexual intercourse by injection means.

5. The method as described in claims 1, 2, 3 or 4, wherein said injection means is accomplished by way of the vaginal tract, through the cervix and into the uterus.

6. The method as described by claim 5, wherein the amount of the drug introduced into the uterus is about 10 milligrams or greater.

7. A pregnancy prevention composition comprising an effective amount of N-phenyl-1-naphthylamine and a suitable carrier medium selected from the group consisting of jelly carriers, foam carriers, and paraffin oil, for introducing said drugs directly into the uterus.

8. The composition as described by claim 7, wherein the concentration of N-phenyl-1-naphthylamine is equal to or greater than 5 milligrams per milliliter of said carrier medium.